(12) United States Patent
Viker

(10) Patent No.: US 7,892,285 B2
(45) Date of Patent: Feb. 22, 2011

(54) UNIVERSAL JOINT TOTAL DISC REPLACEMENT

(75) Inventor: Thomas O. Viker, Arden Hills, MN (US)

(73) Assignee: Zimmer Spine, Inc., Minneapolis, MN (US)

(*) Notice: Subject to any disclaimer, the term of this patent is extended or adjusted under 35 U.S.C. 154(b) by 365 days.

(21) Appl. No.: 11/619,028

(22) Filed: Jan. 2, 2007

(65) Prior Publication Data
US 2008/0161924 A1  Jul. 3, 2008

(51) Int. Cl.
*A61F 2/44* (2006.01)

(52) U.S. Cl. .............. 623/17.13; 623/17.11; 623/17.16; 606/249

(58) Field of Classification Search .............. 606/61, 606/60, 246–249, 279; 623/17.11–17.16; 267/161
See application file for complete search history.

(56) References Cited

U.S. PATENT DOCUMENTS

| | | | |
|---|---|---|---|
| 4,309,777 A | 1/1982 | Patil | |
| 5,401,269 A | 3/1995 | Buttner-Janz et al. | |
| 5,534,030 A | 7/1996 | Navarro et al. | |
| 7,083,651 B2 | 8/2006 | Diaz et al. | |
| 2002/0128714 A1* | 9/2002 | Manasas et al. | 623/17.15 |
| 2004/0204763 A1* | 10/2004 | Ralph et al. | 623/17.13 |
| 2005/0278028 A1 | 12/2005 | Mujwid | |
| 2006/0004453 A1 | 1/2006 | Bartish, Jr. et al. | |
| 2006/0293752 A1* | 12/2006 | Moumene et al. | 623/17.13 |
| 2007/0123990 A1* | 5/2007 | Sharifi-Mehr | 623/17.16 |
| 2007/0168034 A1* | 7/2007 | Kim et al. | 623/17.13 |
| 2008/0215153 A1* | 9/2008 | Butterman et al. | 623/17.16 |

* cited by examiner

*Primary Examiner*—Eduardo C Robert
*Assistant Examiner*—Christina Negrelli
(74) *Attorney, Agent, or Firm*—Seager, Tufte & Wickhem, LLC

(57) ABSTRACT

A vertebral disc replacement includes superior and inferior end plates separated by a leaf spring. The leaf spring includes two opposed legs that extend from a floating intermediate portion of the leaf spring to the superior end plate and two opposed legs that extend from the floating intermediate portion to the inferior end plate. The disc replacement device is compact and provides freedom of movement along three axes, translational along the caudal/cranial axis, lateral bending and flexion/extension.

18 Claims, 4 Drawing Sheets

UNIVERSAL JOINT TOTAL DISC REPLACEMENT

FIELD OF THE INVENTION

The present invention relates to a prosthetic intravertebral disc used to replace a diseased natural disc.

BACKGROUND OF THE INVENTION

Vertebral discs separate adjacent vertebral bodies and allow for relative movement between the adjacent vertebral bodies. Disease, trauma and the like, can cause deterioration of these natural discs, eventually requiring removal of the diseased or damaged disc. In certain circumstances, the disc is removed and the adjoining vertebral bodies fused. Alternately, the natural disc can be replaced with a prosthetic disc.

There are a wide variety of prosthetic discs. Many of these use a ball joint type mechanism, such as disclosed in Buttner-Janz et al., U.S. Pat. No. 5,401,269 and Diaz et al., U.S. Pat. No. 7,083,651. Other replacement discs are disclosed in Navarro et al., U.S. Pat. No. 5,534,030 and Patil, U.S. Pat. No. 4,309,777, and Bartish, Jr., et al., U.S. Published application No. 2006/0004453. Such devices may suffer from a variety of different problems such as excessive height, lack of resistance to bending, fixed axes of rotation, wear debris, and revision complications and risks.

Accordingly, there is a need for an improved prosthetic disc that overcomes these problems associated with known prosthetic discs.

SUMMARY OF THE INVENTION

The present invention overcomes the foregoing and other shortcomings and drawbacks of prosthetic intravertebral discs heretofore known. While the invention will be described in connection with certain embodiments, it will be understood that the invention is not limited to these embodiments. On the contrary, the invention includes all alternatives, modifications and equivalents as may be included within the spirit and scope of the present invention.

The present invention is premised on the realization that a prosthetic disc having inferior and superior end plates separated by a U-joint leaf spring provides a superior prosthetic disc. Preferably, the leaf spring has four opposed legs, two inferior extending legs and two superior extending legs. The legs extend from a floating intermediate portion located between the inferior and superior end plates. This provides at least three degrees of freedom relative to one another, translational along the caudal/cranial axis; lateral bending; and flexion/extension.

Additionally, translation is made available in the horizontal plane provided the legs of the leaf springs include vertical loops. Rotation in the horizontal plane can be provided by employing separate upper and lower interconnected leaf springs. The device is symmetrical about the midsagittal plane, providing balance and resistance to lateral bending. The prosthetic disc can be designed to either provide a cervical disc replacement or a lumbar disc replacement. Further, the prosthetic disc is compact and can be inserted with a compressing device which allows for placement of the compressed disc between adjacent vertebral bodies, and, if necessary, recompression and repositioning of the disc.

One embodiment of the present invention allows placement of a fusion mass between the end plates, if subsequent stabilization is required.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
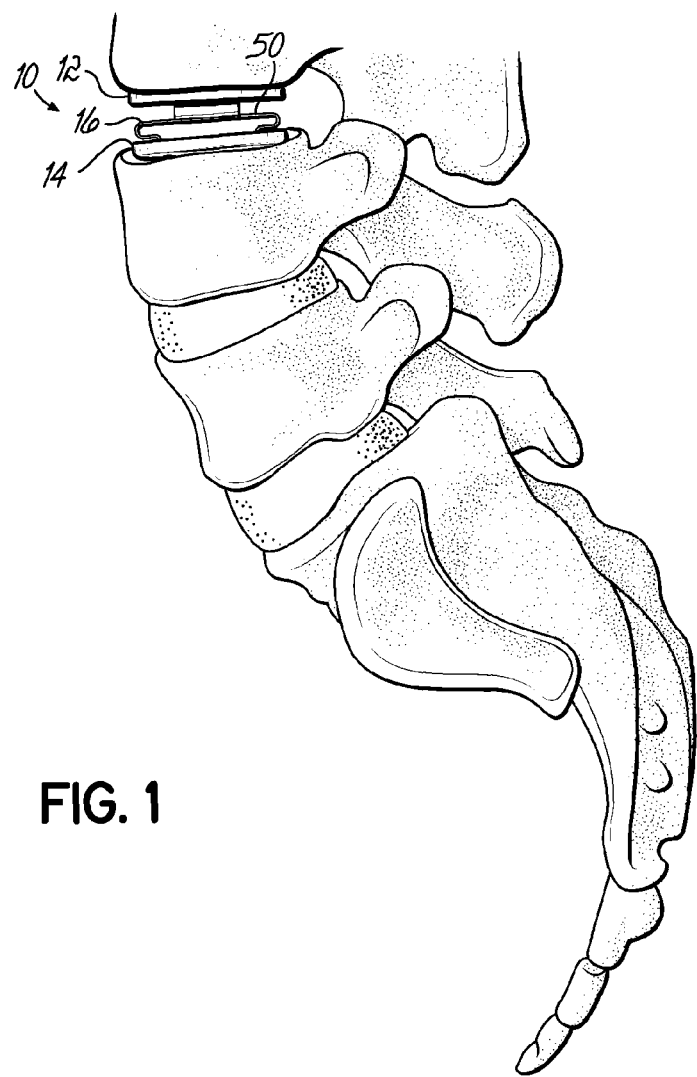
FIG. 1 is an elevational view partially broken away of a vertical column having an artificial disc of the present invention placed therein.
Figure 2:
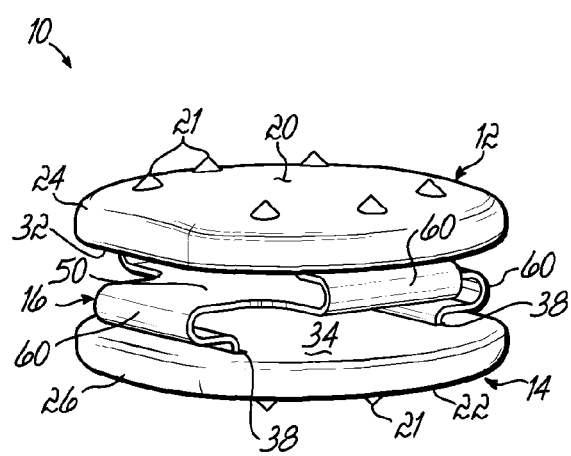
FIG. 2 is a perspective view of the replacement vertebral disc of the present invention.

As shown in FIGS. 1 and 2, a disc replacement 10 is shown in accordance with one embodiment of the present invention and includes a superior end plate 12, an inferior end plate 14, and a U-joint leaf spring 16 positioned between the superior and inferior end plates 12, 14. Both the superior end plate 12 and inferior end plate 14 may include convex exterior surfaces 20 and 22, each surface including a plurality of conical projections 21. Likewise, the end plates 12 and 14 may include chamfered edges 24 and 26, which assist in compression of the disc for insertion as discussed hereinafter.

Figure 3:
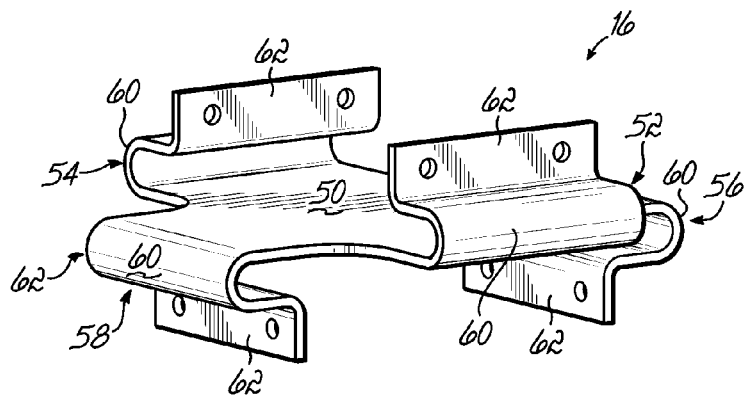
FIG. 3 is a perspective view of the U-joint leaf spring used in the preferred embodiment of the present invention.
Figure 4:
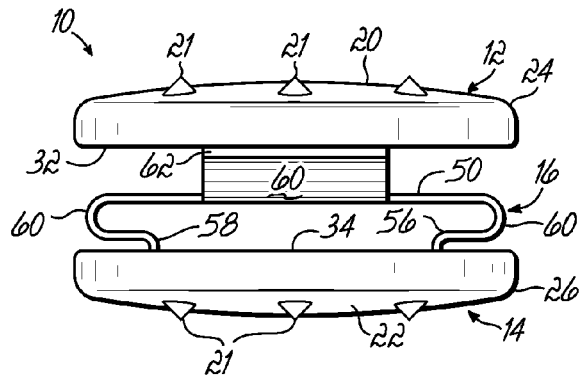
FIG. 4 is an elevational view of the first side of the vertebral disc of the present invention.
Figure 5:
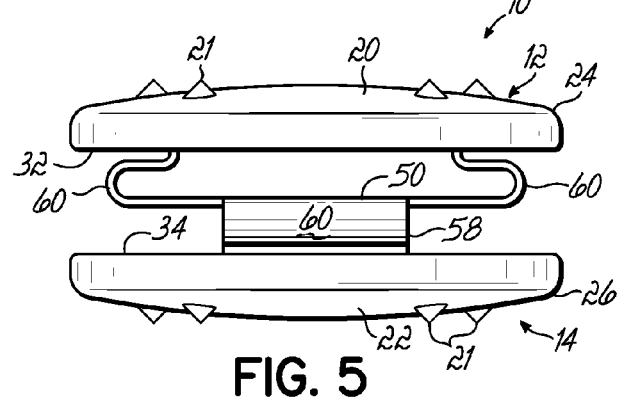
FIG. 5 is an elevational anterior view of the vertebral disc of the present invention.
Figure 6:
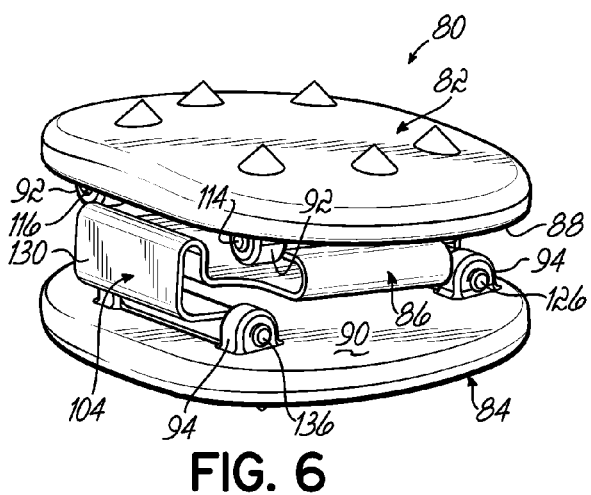
FIG. 6 is a perspective view of an alternate embodiment of the present invention.
Figure 7:
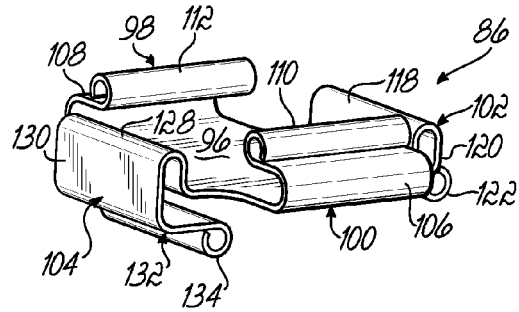
FIG. 7 is a perspective view of the leaf spring used in the embodiment shown in FIG. 6.
Figure 8:
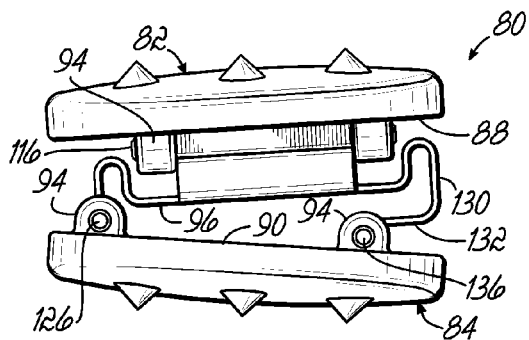
FIG. 8 is a first side elevational view of the alternate embodiment of FIG. 6.
Figure 9:
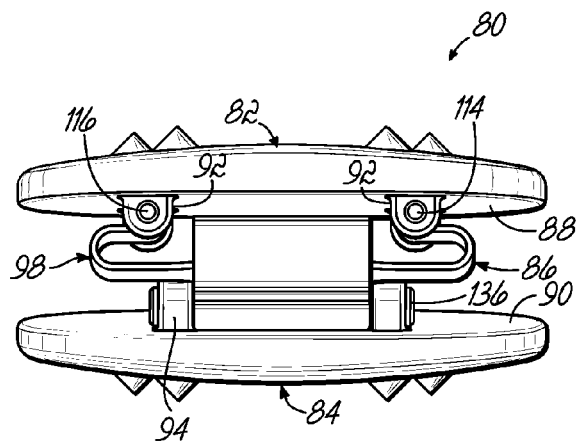
FIG. 9 is an elevational anterior view of the embodiment shown in FIG. 6.

As shown in FIGS. 1-3, the U-joint leaf spring 16 includes a floating intermediate portion 50. In one embodiment, the intermediate portion 50 may be generally planar. Opposed superior legs 52 and 54 extend from the intermediate portion 50 into slots (not shown) formed in the interior surface 32 of the superior end plate 12. Spring 16 further includes opposed inferior legs 56 and 58, which extend from the intermediate portion 50 to slots 38 (one shown in FIG. 2) formed in the interior surface 34 of the inferior end plate 14. Each of the legs 52, 54, 56 and 58 includes a 180 degree vertical loop 60. Each leg terminates in a terminal flange 62 which lodges in a respective slot formed in the interior surfaces 32 and 34 of end plates 12 and 14.

The flanges 62 can be fixed in slots 38 by a variety of different mechanisms such as, by way of an example, an adhesive, an interference fit such as a barbed interference fit, or they can be molded in situ to the end of plates 12, and 14.

The superior and inferior end plates 12 and 14 are formed from any material which can withstand application stresses for location within the body. These can include polymers, ceramics or metals. They may have surface texture or coating to promote boney ingrowth, as is well known. In one embodiment, the joint leaf spring 16 is formed from stainless steel, although any suitable material is possible as well.

Figure 12:
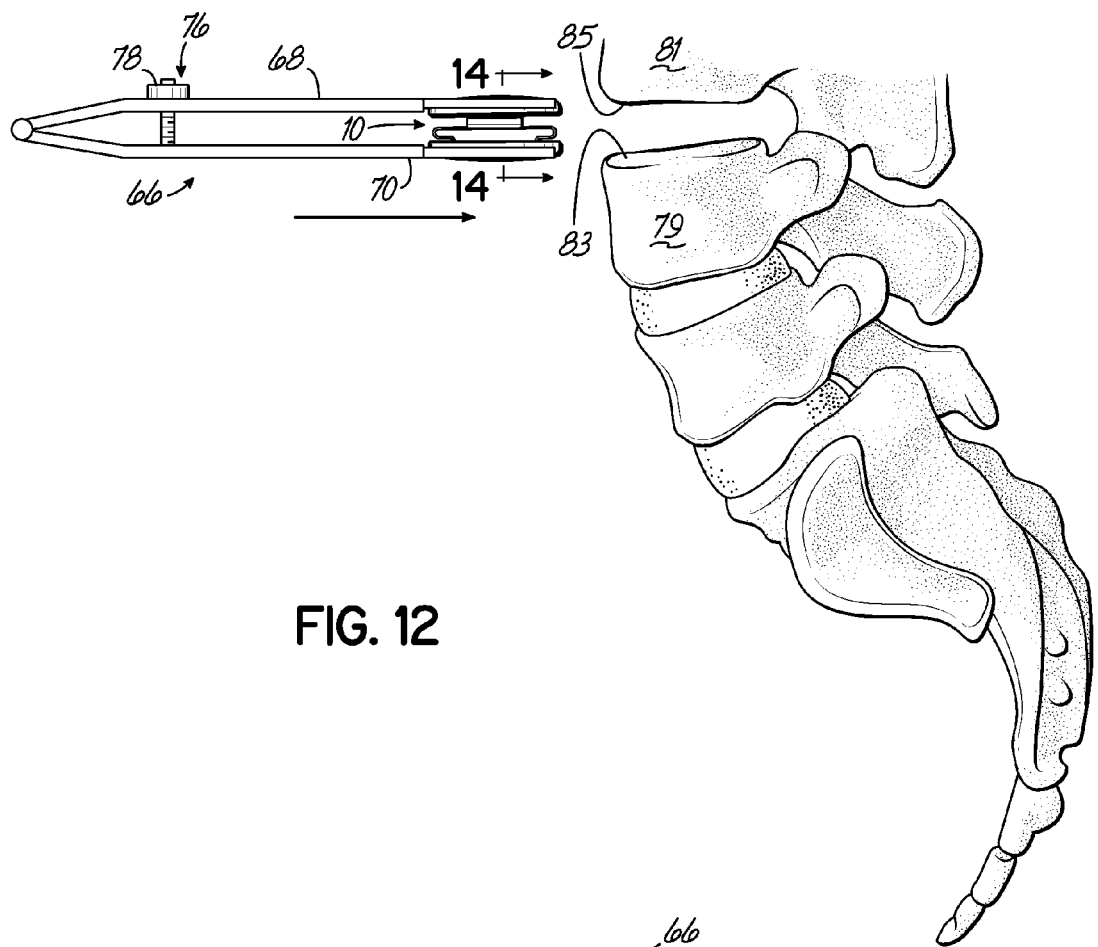
FIG. 12 is a diagrammatic view depicting the method of inserting the replacement vertebral disc of the present invention.
Figure 13:
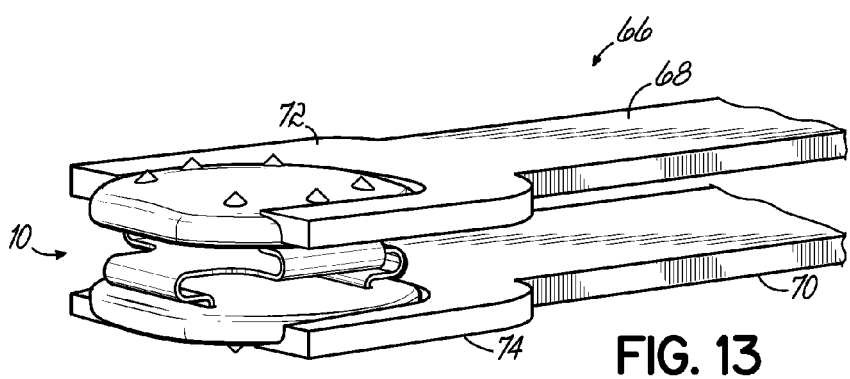
FIG. 13 is a diagrammatic view partially broken away showing a tool used to insert the disc.
Figure 14:
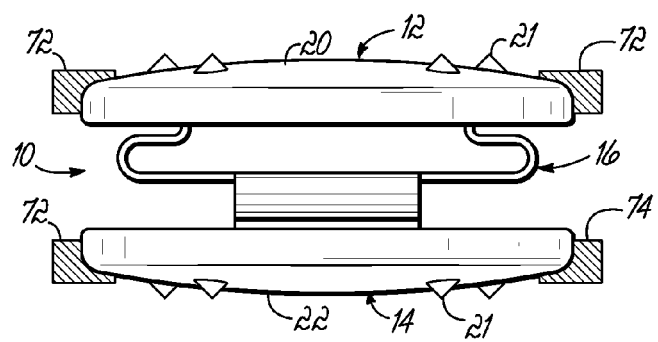
FIG. 14 is a cross sectional view taken at line 14-14 of FIG. 12.

To insert the disc 10, the disc space is prepared by performing a complete discectomy, followed by distraction. The implant 10 is compressed by a device as shown in FIGS. 12-14. As shown, compressor 66 includes arms 68 and 70. Each arm has a C-shaped end 72 and 74. The arms are separated by a threaded pin 76 fixed to arm 70 and extended through a hole in arm 68. An internally threaded tightener 78 rotates on pin 76 to compress the arms. The C-shaped ends 72 and 74 are adapted to engage the chamfered edges 24 and 26 of end plates 12 and 14. As the tightener 78 is rotated, the arms 68 and 70 are compressed and the end plates 12 and 14 of the disc 10 compress the spring 16. As shown in FIG. 12, the compressed disc 10 is positioned between the vertical bodies 79, 81 and the tightener 78 is then loosened allowing the end plates 12 and 14 to engage the surfaces 83 and 85 of adjacent vertebral bodies. The conical projections 21 will engage the surfaces 83, 85 of the vertebral bodies 79, 81 holding the disc 10 in position within the disc space. If necessary, the compressor 66 can engage an already positioned disc 10 and recompress this so the device can be repositioned.

A first alternative embodiment of the present invention is shown in FIGS. 6-9, which show a replacement disc 80 that is particularly designed for lumbar replacements. The lumbar replacement disc 80 includes a superior end plate 82 and an inferior end plate 84 separated by a U-joint leaf spring 86. The end plates include interior surfaces 88 and 90, which each include opposed sets of protrusions or bosses 92 and 94.

The U-joint leaf spring 86 includes a floating intermediate portion 96 with superior extended legs 98 and 100, and a posterior inferior extended leg 102 and an anterior inferior extended leg 104. The superior legs 98 and 100 both include a 180 degree vertical loop 106 and 108. The legs 98 and 100 terminate at cylinders 110 and 112 which are connected to protrusions 92 utilizing pins 114 and 116.

The posterior inferior leg 102 includes a vertical 180 degree loop 118, which extends back to a vertical portion 120 extending to an end cylinder 122. This is rotatably attached by a pin 126 to protrusions 94. The anterior inferior leg 104 includes a vertical loop 128, which extends to a vertical portion 130. The vertical portion 130 extends to a horizontal loop 132 that terminates in an end cylinder 134. The end cylinder 134 rotatably attaches to the protrusions 94 by a pin 136. The additional loops in the posterior and anterior inferior extended legs provide for fore/aft translation to provide positional flexibility of flexion extension bend axes. In particular, the additional bends in the anterior inferior leg prevent stress concentration. This structure can be implanted in the same manner as the replacement disc 10 previously described.

Figure 10:
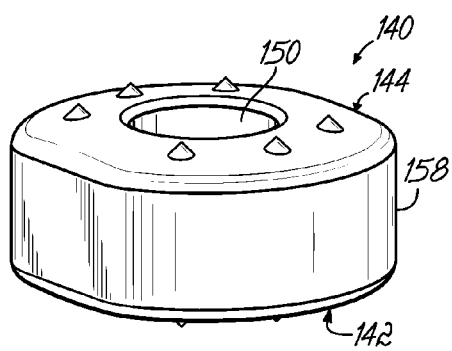
FIG. 10 is a perspective view of a third embodiment of the present invention.
Figure 11:
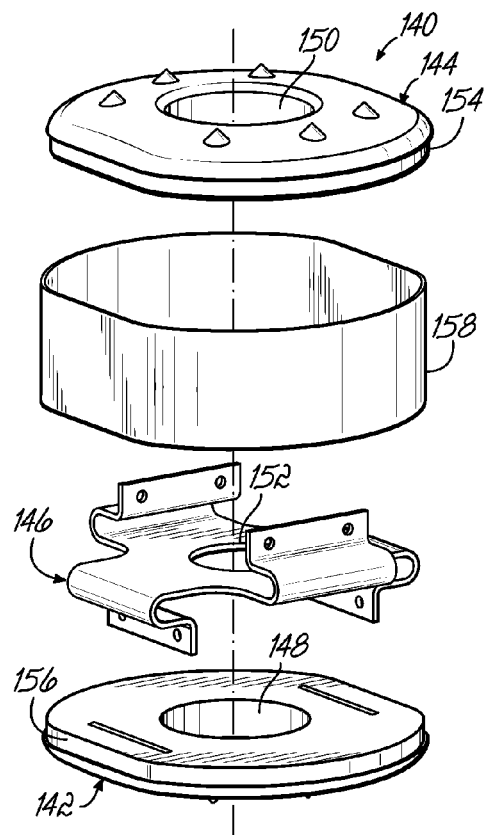
FIG. 11 is an exploded view of the embodiment shown in FIG. 10.

A second alternative embodiment of the present invention is shown in FIG. 10. In this embodiment, the disc replacement 140 includes inferior and superior end plates 142 and 144 connected together by U-joint leaf spring 146. This is assembled in the same manner as the embodiment shown in FIG. 1. Any leaf spring configuration such as that shown in FIG. 3 or FIG. 6 can be employed. The end plates 142 and 144 each include an opening 148, 150. Likewise, U-joint spring member 146 includes an opening 152. Both the upper and lower end plates 142 and 144 include rims 154 and 156. When assembled, a fabric curtain 158 may be heat welded, adhered or otherwise joined to the end plates 142 and 144 along rims 154 and 156.

This device 140 would be inserted in the same manner as the device 10. However, this device provides an added benefit in the event a revision strategy is required. The disc replacement 140 as shown in FIG. 10 can be fused because of the open structure of the device. This allows a packing material to be forced into the interior of the device connecting the adjacent end plates 142, 146. The fabric curtain 158 within the end plates will enclose the interior. This allows a posterior approach fusion procedure which can be achieved without removing the device. Further stabilization can be effected with a pedicle screw system or other posterior instrumentation.

The present invention provides a variety of different advantages. Due to the design, the device should have a long life with minimal wear debris. Thus, the present invention provides a wide variety of advantages vis-à-vis prior replacement discs.

Further, the replacement disc of the present invention is very compact, reducing the tendency to over distract. It provides resistance to flexion, extension and lateral bending, similar to the natural anatomy. Further, the floating axis of rotation protects facet joints.

The tortional rigidity of the present invention is preferable to uncontrolled tortional freedom. Further, the cushioning in the caudal/cranial axis isolates impulses from end plates. The device provides the possibility to carry a tension load in the caudal/cranial axis after bone on growth prevents lift off of device from vertebral end plates.

As previously noted, due to the open nature of this product it provides a safe revision strategy. As these devices are typically implanted from the anterior side, due to the open nature of these products, a posterior approach fusion procedure can be utilized without removing the device.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, I claim:

1. A disc replacement comprising:
    a superior end plate;
    an inferior end plate; and
    a leaf spring having an intermediate unitary floating portion, a pair of first and second superior legs each connected between the unitary floating portion and the superior plate, and a pair of first and second inferior legs each connected between the unitary floating portion and the inferior plate; wherein the intermediate unitary floating portion of the leaf spring is spaced apart from both the superior end plate and the inferior end plate, the unitary floating portion attached to the superior and inferior end plates via the superior and inferior legs, respectively;

wherein the first and second superior legs each include a 180 degree loop and wherein the first and second inferior legs each include a 180 degree loop, wherein the 180 degree loops are spaced apart from the superior and inferior end plates, wherein the inferior legs are separated by 180degrees and the superior extended legs are separated by 180 degrees.

2. The disc replacement of claim 1, wherein the inferior legs are separated from said superior legs by 90 degrees.

3. The disc replacement of claim 1, wherein at least one of the superior end plate and the inferior end plate includes an exterior surface having a convex shape.

4. The disc replacement of claim 1, wherein said 180 degree loops are horizontal loops.

5. The disc replacement of claim 1, wherein intermediate unitary floating portion of the spring comprises a generally planar portion.

6. The disc replacement of claim 5, wherein each of the superior end plates and the inferior end plates includes a chamfered edge.

7. A combination of the disc replacement of claim 1 with a compressing device, the compressing device having first and second arms each having a C-shaped end configured to engage peripheral edges of the superior end plate and the inferior end plate, wherein the arms are configured to be urged together to compress the superior and inferior end plates together.

8. The disc replacement of claim 1, wherein at least one of the 180 degree loops is a vertical loop.

9. The disc replacement of claim 8, wherein the superior legs each include a vertical loop and at least one of the inferior legs includes a horizontal loop.

10. The disc replacement of claim 8, wherein the inferior and superior legs terminate in respective cylinders which are rotatably attached to the inferior and superior end plates.

11. The disc replacement of claim 1, wherein the inferior and superior legs terminate in respective flanges embedded in the superior and inferior end plates.

12. A disc replacement comprising:
a superior end plate;
an inferior end plate; and
a leaf spring having an intermediate unitary floating portion, a pair of first and second superior legs each connected between the unitary floating portion and the superior plate, and a pair of first and second inferior legs each connected between the unitary floating portion and the inferior plate; wherein the intermediate unitary floating portion of the leaf spring is spaced apart from both the superior end plate and the inferior end plate, the unitary floating portion attached to the superior and inferior end plates via the superior and inferior legs, respectively; wherein the first and second superior legs each include a 180 degree loop and wherein the first and second inferior legs each include a 180 degree loop, wherein the 180 degree loops are spaced apart from the superior and inferior end plates, wherein the superior and inferior end plates and the spring each include an opening extending vertically therethrough.

13. The disc replacement of claim 12, wherein the disc replacement includes a skirt extended between and substantially enclosing the area between the inferior and superior end plates.

14. A disc replacement comprising:
a superior end plate;
an inferior end plate; and
a leaf spring having an intermediate floating portion, a pair of first and second superior legs each connected between the floating portion and the superior plate, and a pair of first and second inferior legs each connected between the floating portion and the inferior plate; wherein the leaf spring with first and second superior legs and first and second inferior legs is a unitary element and is not integral with the superior and inferior end plates; wherein the intermediate floating portion of the leaf spring is spaced apart from the superior and inferior end plates, wherein the inferior and superior legs terminate in respective flanges embedded in the superior and inferior end plates.

15. The disc replacement of claim 14, wherein the first and second superior legs each include a 180 degree loop and wherein the first and second inferior legs each include a 180 degree loop, wherein the 180 degree loops are spaced apart from the superior and inferior end plates.

16. The disc replacement of claim 15, wherein at least one of the 180 degree loops is a vertical loop.

17. The disc replacement of claim 16, wherein the superior legs each include a vertical loop and at least one of the inferior legs includes a horizontal loop.

18. The disc replacement of claim 17, wherein the inferior and superior legs terminate in respective cylinders which are rotatably attached to the inferior and superior end plates.

* * * * *